(12) United States Patent
Chanduszko et al.

(10) Patent No.: US 9,017,373 B2
(45) Date of Patent: Apr. 28, 2015

(54) SEPTAL CLOSURE DEVICES

(75) Inventors: Andrzej J. Chanduszko, Weymouth, MA (US); Carol A. Devellian, Topsfield, MA (US); Todd A. Peavey, Cambridge, MA (US); David Widomski, Wakefield, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 586 days.

(21) Appl. No.: 10/731,547

(22) Filed: Dec. 9, 2003

(65) Prior Publication Data

US 2004/0176799 A1 Sep. 9, 2004

Related U.S. Application Data

(60) Provisional application No. 60/431,924, filed on Dec. 9, 2002.

(51) Int. Cl.
 *A61B 17/08* (2006.01)
 *A61B 17/00* (2006.01)

(52) U.S. Cl.
 CPC ... *A61B 17/0057* (2013.01); *A61B 2017/00004* (2013.01); *A61B 2017/00575* (2013.01); *A61B 2017/00592* (2013.01); *A61B 2017/00606* (2013.01); *A61B 2017/00619* (2013.01); *A61B 2017/00867* (2013.01)

(58) Field of Classification Search
 USPC .......... 606/213, 216, 215, 94, 157, 151, 153, 606/158, 194, 198, 200; 600/37; 604/96.01, 604/101.5, 107, 108, 109; 623/1.1, 1.12, 623/1.16; 128/899
 See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |

(Continued)

FOREIGN PATENT DOCUMENTS

| | | |
|---|---|---|
| DE | 9413645 U1 | 10/1994 |
| EP | 0362113 A1 | 4/1990 |

(Continued)

OTHER PUBLICATIONS

Nat'l Aeronautics and Space Administration, "55-Nitinol—The Alloy with a Memory: Its Physical Metallurgy, Properties, and Applications," A Report, pp. 24-25.

(Continued)

*Primary Examiner* — Dianne Dornbusch
*Assistant Examiner* — Robert Lynch
(74) *Attorney, Agent, or Firm* — DLA Piper LLP (US)

(57) ABSTRACT

A closure device for a patent foramen ovale (PFO) has proximal and distal occlusion members for applying compressive forces to tissue on opposite sides of septal defects to help close the defects. The devices are collapsible for delivery and deployment, and can be easily retrieved and redeployed or repositioned if needed.

17 Claims, 10 Drawing Sheets

(56) References Cited

U.S. PATENT DOCUMENTS

| | | | |
|---|---|---|---|
| 4,693,249 A | 9/1987 | Schenck et al. | |
| 4,696,300 A | 9/1987 | Anderson | |
| 4,710,181 A | 12/1987 | Fuqua | |
| 4,710,192 A | 12/1987 | Liotta et al. | |
| 4,738,666 A | 4/1988 | Fuqua | |
| 4,832,055 A * | 5/1989 | Palestrant | 128/899 |
| 4,836,204 A | 6/1989 | Landymore et al. | |
| 4,840,623 A | 6/1989 | Quackenbush | |
| 4,902,508 A | 2/1990 | Badylak et al. | |
| 4,915,107 A | 4/1990 | Rebuffat et al. | |
| 4,917,089 A | 4/1990 | Sideris | |
| 4,921,479 A | 5/1990 | Grayzel | |
| 4,956,178 A | 9/1990 | Badylak et al. | |
| 5,021,059 A | 6/1991 | Kensey et al. | |
| 5,037,433 A | 8/1991 | Wilk et al. | 606/139 |
| 5,041,129 A | 8/1991 | Hayhurst et al. | |
| 5,049,131 A | 9/1991 | Deuss | |
| 5,078,736 A | 1/1992 | Behl | |
| 5,106,913 A | 4/1992 | Yamaguchi et al. | |
| 5,108,420 A | 4/1992 | Marks | |
| 5,149,327 A | 9/1992 | Oshiyama et al. | |
| 5,163,131 A | 11/1992 | Row et al. | |
| 5,167,363 A | 12/1992 | Adkinson et al. | |
| 5,167,637 A | 12/1992 | Okada et al. | |
| 5,171,259 A | 12/1992 | Inoue | |
| 5,176,659 A | 1/1993 | Mancini | |
| 5,192,301 A | 3/1993 | Kamiya et al. | |
| 5,222,974 A | 6/1993 | Kensey et al. | |
| 5,226,879 A | 7/1993 | Ensminger et al. | |
| 5,236,440 A | 8/1993 | Hlavacek | |
| 5,245,023 A | 9/1993 | Peoples et al. | |
| 5,245,080 A | 9/1993 | Aubard et al. | |
| 5,250,430 A | 10/1993 | Peoples et al. | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,316,262 A | 5/1994 | Koebler | |
| 5,320,611 A | 6/1994 | Bonutti et al. | |
| 5,334,217 A | 8/1994 | Das | |
| 5,350,363 A | 9/1994 | Goode et al. | |
| 5,354,308 A | 10/1994 | Simon et al. | |
| 5,364,356 A | 11/1994 | Hofling | |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,453,099 A | 9/1995 | Lee et al. | |
| 5,478,353 A | 12/1995 | Yoon | |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,534,432 A | 7/1996 | Peoples et al. | |
| 5,540,712 A | 7/1996 | Kleshinski et al. | |
| 5,562,632 A | 10/1996 | Davila et al. | |
| 5,577,299 A | 11/1996 | Thompson et al. | |
| 5,601,571 A | 2/1997 | Moss | |
| 5,603,703 A | 2/1997 | Elsberry et al. | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A | 12/1997 | Schneidt et al. | |
| 5,709,707 A | 1/1998 | Lock et al. | |
| 5,713,864 A | 2/1998 | Verkaart | |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A * | 3/1998 | Forber et al. | 606/151 |
| 5,733,337 A | 3/1998 | Carr, Jr. et al. | |
| 5,741,297 A | 4/1998 | Simon | |
| 5,772,641 A | 6/1998 | Wilson | |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,516 A | 9/1998 | Fine et al. | |
| 5,810,884 A | 9/1998 | Kim | |
| 5,820,594 A | 10/1998 | Fontirroche et al. | |
| 5,823,956 A | 10/1998 | Roth et al. | |
| 5,829,447 A | 11/1998 | Stevens et al. | |
| 5,853,420 A | 12/1998 | Chevillon et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A | 4/1999 | Jacob et al. | |
| 5,902,287 A | 5/1999 | Martin | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | 128/898 |
| 5,928,250 A | 7/1999 | Koike et al. | |
| 5,944,691 A | 8/1999 | Querns et al. | |
| 5,944,738 A | 8/1999 | Amplatz et al. | |
| 5,955,110 A | 9/1999 | Patel et al. | |
| 5,976,174 A * | 11/1999 | Ruiz | 606/213 |
| 5,980,505 A | 11/1999 | Wilson | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,019,753 A | 2/2000 | Pagan | |
| 6,024,756 A | 2/2000 | Huebsch et al. | |
| 6,027,519 A | 2/2000 | Stanford | |
| 6,030,007 A | 2/2000 | Bassily et al. | |
| 6,056,760 A | 5/2000 | Koike et al. | 606/148 |
| 6,071,998 A | 6/2000 | Muller et al. | |
| 6,077,291 A | 6/2000 | Das | 606/213 |
| 6,077,880 A | 6/2000 | Castillo et al. | |
| 6,079,414 A | 6/2000 | Roth | 128/898 |
| 6,080,182 A | 6/2000 | Shaw et al. | 606/213 |
| 6,096,347 A | 8/2000 | Geddes et al. | |
| 6,106,913 A | 8/2000 | Scardino et al. | |
| 6,113,609 A | 9/2000 | Adams | 606/144 |
| 6,117,159 A * | 9/2000 | Huebsch et al. | 606/213 |
| 6,126,686 A | 10/2000 | Badylak et al. | |
| 6,132,438 A | 10/2000 | Fleischman et al. | 606/139 |
| 6,143,037 A | 11/2000 | Goldstein et al. | |
| 6,152,144 A | 11/2000 | Lesh et al. | |
| 6,165,183 A | 12/2000 | Kuehn et al. | 606/139 |
| 6,165,204 A | 12/2000 | Levinson et al. | 606/232 |
| 6,168,588 B1 | 1/2001 | Wilson | |
| 6,171,329 B1 * | 1/2001 | Shaw et al. | 606/213 |
| 6,174,322 B1 | 1/2001 | Schneidt | 606/213 |
| 6,174,330 B1 | 1/2001 | Stinson | |
| 6,183,443 B1 | 2/2001 | Kratoska et al. | |
| 6,187,039 B1 | 2/2001 | Hiles et al. | |
| 6,190,353 B1 | 2/2001 | Makower et al. | |
| 6,190,357 B1 | 2/2001 | Ferrari et al. | |
| 6,197,016 B1 | 3/2001 | Fourkas et al. | |
| 6,199,262 B1 | 3/2001 | Martin | |
| 6,206,895 B1 | 3/2001 | Levinson | 606/144 |
| 6,206,907 B1 | 3/2001 | Marino et al. | 606/215 |
| 6,214,029 B1 | 4/2001 | Thill et al. | 606/213 |
| 6,217,590 B1 | 4/2001 | Levinson | 606/142 |
| 6,221,092 B1 | 4/2001 | Koike et al. | 606/213 |
| 6,227,139 B1 | 5/2001 | Nguyen et al. | |
| 6,228,097 B1 | 5/2001 | Levinson et al. | 606/142 |
| 6,231,561 B1 | 5/2001 | Frazier et al. | |
| 6,245,080 B1 | 6/2001 | Levinson | 606/144 |

(56) References Cited

U.S. PATENT DOCUMENTS

| | | |
|---|---|---|
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. ................ 606/213 |
| 6,277,138 B1 | 8/2001 | Levinson et al. ............ 606/200 |
| 6,277,139 B1 | 8/2001 | Levinson et al. ............ 606/200 |
| 6,287,317 B1 | 9/2001 | Makower et al. ............ 606/153 |
| 6,290,674 B1 | 9/2001 | Roue et al. .................... 604/107 |
| 6,299,635 B1 | 10/2001 | Frantzen |
| 6,306,150 B1 | 10/2001 | Levinson ..................... 606/158 |
| 6,306,424 B1 | 10/2001 | Vyakarnam et al. |
| 6,312,443 B1 | 11/2001 | Stone |
| 6,312,446 B1 | 11/2001 | Huebsch et al. ............. 606/213 |
| 6,315,791 B1 | 11/2001 | Gingras et al. |
| 6,316,262 B1 | 11/2001 | Huisman et al. |
| 6,319,263 B1 | 11/2001 | Levinson ..................... 606/144 |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. ................. 606/213 |
| 6,344,048 B1 | 2/2002 | Chin et al. |
| 6,344,049 B1 | 2/2002 | Levinson et al. ............ 606/200 |
| 6,346,074 B1 | 2/2002 | Roth |
| 6,348,041 B1 | 2/2002 | Klint ........................... 600/585 |
| 6,352,552 B1 | 3/2002 | Levinson et al. ............ 623/1.15 |
| 6,355,052 B1* | 3/2002 | Neuss et al. .................. 606/213 |
| 6,356,782 B1 | 3/2002 | Sirimanne et al. |
| 6,358,238 B1 | 3/2002 | Sherry |
| 6,364,853 B1 | 4/2002 | French et al. .................. 604/35 |
| 6,371,904 B1 | 4/2002 | Sirimanne et al. |
| 6,375,625 B1 | 4/2002 | French et al. ................ 600/573 |
| 6,375,671 B1 | 4/2002 | Kobayashi et al. .......... 606/213 |
| 6,379,342 B1 | 4/2002 | Levinson ..................... 604/310 |
| 6,379,368 B1 | 4/2002 | Corcoran et al. ............ 606/153 |
| 6,387,104 B1 | 5/2002 | Pugsley, Jr. et al. .......... 606/139 |
| 6,398,796 B2 | 6/2002 | Levinson ..................... 606/144 |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. ................. 606/213 |
| 6,450,987 B1 | 9/2002 | Kramer |
| 6,460,749 B1 | 10/2002 | Levinson et al. .......... 227/180.1 |
| 6,482,224 B1 | 11/2002 | Michler et al. |
| 6,488,706 B1 | 12/2002 | Solymar ........................ 623/3.1 |
| 6,494,846 B1 | 12/2002 | Margolis |
| 6,494,888 B1 | 12/2002 | Laufer et al. ................. 606/153 |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,719 B2 | 7/2003 | Wang |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,506 B2* | 9/2003 | McGuckin et al. ........... 606/200 |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 7,097,653 B2* | 8/2006 | Freudenthal et al. ......... 606/213 |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Borillo et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0113868 A1 | 6/2003 | Flor et al. |
| 2003/0120337 A1 | 6/2003 | Van Tassel et al. |
| 2003/0139819 A1 | 7/2003 | Beer et al. |
| 2003/0171774 A1 | 9/2003 | Freudenthal et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0133236 A1 | 7/2004 | Chanduszko |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0113868 A1 | 5/2005 | Devellian |
| 2005/0267523 A1 | 12/2005 | Devellian et al. |
| 2005/0273135 A1 | 12/2005 | Chanduszko et al. |
| 2005/0288786 A1 | 12/2005 | Chanduszko |
| 2006/0122647 A1 | 6/2006 | Callaghan et al. |
| 2006/0265004 A1 | 11/2006 | Callaghan et al. |
| 2006/0271089 A1 | 11/2006 | Alejandro et al. |
| 2007/0010851 A1 | 1/2007 | Chanduszko et al. |
| 2007/0167981 A1 | 7/2007 | Opolski |

(56) References Cited

U.S. PATENT DOCUMENTS

FOREIGN PATENT DOCUMENTS

| EP | 0474887 A1 | 3/1992 | |
|---|---|---|---|
| EP | 0 839 549 | 5/1998 | |
| EP | 0 861 632 | 9/1998 | |
| EP | 1 013 227 | 6/2000 | ............ A61B 17/00 |
| EP | 1 046 375 | 10/2000 | |
| EP | 1 222 897 | 7/2002 | |
| WO | WO 96/01591 A1 | 1/1996 | |
| WO | WO 96/25179 | 8/1996 | |
| WO | WO 96/31157 | 10/1996 | |
| WO | WO-98/07375 A1 | 2/1998 | |
| WO | WO-98/08462 | 3/1998 | |
| WO | WO-98/16174 | 4/1998 | |
| WO | WO-98/29026 A2 | 7/1998 | |
| WO | WO-98/51812 | 11/1998 | |
| WO | WO-99/05977 | 2/1999 | |
| WO | WO-98/18864 | 4/1999 | |
| WO | WO-99/18862 A1 | 4/1999 | |
| WO | WO-99/18864 A1 | 4/1999 | |
| WO | WO-99/18870 A1 | 4/1999 | |
| WO | WO-99/18871 A1 | 4/1999 | |
| WO | WO-99/30640 | 6/1999 | |
| WO | WO-99/66846 | 12/1999 | |
| WO | WO 00/27292 A1 | 5/2000 | |
| WO | WO 00/44428 | 8/2000 | |
| WO | WO-01/08600 | 2/2001 | |
| WO | WO-01/19256 | 3/2001 | |
| WO | WO-01/21247 | 3/2001 | |
| WO | WO-01/28432 | 4/2001 | |
| WO | WO-01/30268 | 5/2001 | |
| WO | 01/49185 | 7/2001 | ............ A61B 17/00 |
| WO | WO-01/78596 | 10/2001 | |
| WO | WO-01/93783 | 12/2001 | |
| WO | WO-02/17809 | 3/2002 | |
| WO | WO 02/24106 | 3/2002 | |
| WO | WO-03/024337 | 3/2003 | |
| WO | WO-03/053493 A1 | 7/2003 | |
| WO | WO-03/059152 | 7/2003 | |
| WO | WO-03/063732 A | 8/2003 | |
| WO | WO 03/077733 | 9/2003 | |
| WO | WO-03/082076 | 10/2003 | |
| WO | WO-03/103476 A2 | 12/2003 | |
| WO | WO-2004/032993 | 4/2004 | |
| WO | WO-2004/043266 | 5/2004 | |
| WO | WO-2004/043508 | 5/2004 | |
| WO | WO-2004/052213 | 6/2004 | |
| WO | WO-2005/006990 | 1/2005 | |
| WO | WO-2005/018728 | 3/2005 | |
| WO | WO-2005/027752 | 3/2005 | |
| WO | WO-2005/074813 | 8/2005 | |
| WO | WO-2005/092203 | 10/2005 | |
| WO | WO-2005/110240 | 11/2005 | |
| WO | WO-2005/112779 | 12/2005 | |
| WO | WO-2006/036837 | 4/2006 | |
| WO | WO-2006/102213 | 9/2006 | |

OTHER PUBLICATIONS

Kimura, A., et al., "Effects of Neutron Irradiation on the Transformation Behavior in Ti-Ni Alloys," Abstract, Proceedings of the Int'l Conf. on Mariensitic Transformations (1992) pp. 935-940.
Ramanathan, G., et al., "Experimental and Computational Methods for Shape Memory Alloys," 15th ASCE Engineering Mechanics Conf., Jun. 2-5, 2003.
Shabalovskaya, S., "Surface, corrosion and biocompatibility aspects of Nitinol as an implant material," Bio-Medical materials and Engineering, (2002) vol. 12, pp. 69-109.
Uchil, J. "Shape Memory Alloys—Characterization Techniques," Pramana—Journal of Physics, (2002) vol. 58, Nos. 5 & 6, pp. 1131-1139.
Stöckel, "Nitinol Medical Devices and Implants," SMST-2000 Conference Proceedings, 2001, pp. 531-541.
SMST-2000, "Proceedings of the International Conference on Shape Memory and Superelastic Technologies," Apr. 30 to May 4, 2000, Asilomar Conference Center.
Ruiz et al. "The Puncture Technique: A New Method for Transcatheter Closure of Patent Foramen Ovale," Catheterization and Cardiovascular Interventions 53, Wiley-Liss, Inc., 2001, pp. 369-372.
International Search Report, International Application No. PCT/US03/17390, mailed on Oct. 6, 2003, 4 pgs.
Athanasion, T., "Coronary Artery Bypass with the Use of a Magnetic Distal Anastomotic Device: Surgical Technique and Preliminary Experience," The Heart Surgery Forum #2004-1024, 2004, 4 pgs.
Bachthaler, M. et al., "Corrosion of Tungsten Coils After Peripheral Vascular Embolization Theraphy: Influence on Outcome and Tungsten Load", Catherization and Cardiovascular Interventions, vol. 62, pp. 380-384, 2004.
European Examination Report, European Application No. 04781644.2, mailed Aug. 23, 2007 (3 Pages).
European Search Report, European Application No. 03729663.9, mailed Feb. 20, 2008 (3 Pages).
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/17715, mailed Mar. 24, 2004 (2 pgs).
International Search Report, International Application No. PCT/US03/32133, mailed Apr. 22, 2004 (1 pg).
International Search Report, International Application No. PCT/US03/34003 mailed Oct. 3, 2004 (4 pgs).
International Search Report, International Application No. PCT/US03/35479, mailed Apr. 14, 2004 (2 pgs).
International Search Report, International Application No. PCT/US03/35998 mailed Jun. 16, 2004 (5 pgs).
International Search Report, International Application No. PCT/US03/39253, mailed Apr. 19, 2004 (4 pgs).
International Search Report, International Application No. PCT/US04/022643, mailed Mar. 31, 2005 (2 pgs).
International Search Report, International Application No. PCT/US04/026998, mailed Apr. 22, 2005 (5 pgs).
International Search Report, International Application No. PCT/US04/029978, mailed Jan. 26, 2005 (3 pgs).
International Search Report, International Application No. PCT/US05/006703, mailed Jul. 25, 2005 (3 pgs).
International Search Report, International Application No. PCT/US05/013705 mailed Aug. 4, 2005 (4 pgs).
International Search Report, International Application No. PCT/US05/015382, mailed Oct. 6, 2005 (4 pgs).
International Search Report, International Application No. PCT/US07/065546, mailed Oct. 29, 2007. 4 pages.
International Search Report, International Application No. PCT/US2007/065526, mailed Aug. 8, 2007 (5 pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
Isotalo, T. et al., "Biocompatibility Testing of a New Bioabsorbable X-Ray Positive SR-PLA 96/4 Urethral Stent", The Journal of Urology, vol. 163, pp. 1764-1767, Nov. 1999.
Klima, U., "Magnetic Vascular Port in Minimally Invasive Direct Coronary Artery Bypass Grafting," Circulation, 2004, II-55-II-60.

(56) References Cited

OTHER PUBLICATIONS

Meier, MD, Bernhard, et al., "Contemporary Management of Patent Foramen Ovale," American Heart Association, Inc., Circulation, 2003, vol. 107, pp. 5-9.

Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.

Ruddy, A.C. et al., "Rheological, Mechanical and Thermal Behaviour of Radipaque Filled Polymers", *Polymer Processing Research Centre*, School of Chemical Engineering, Queen's University of Belfast, 5 pages.

Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

European Examination Report, European Application No. 03729663.9, mailed Jul. 16, 2008 (5 Pages).

European Examination Report, European Application No. 03731562.9, mailed Jul. 18, 2008 (3 Pages).

European Examination Report, European Application No. 03779297.5, mailed Mar. 15, 2007 (6 Pages).

International Search Report and Written Opinion, International Patent Application No. PCT/US06/41255, mailed Jun. 13, 2008 (6 pgs).

International Search Report and Written Opinion, International Patent Application No. PCT/US08/59429, mailed Sep. 5, 2008 (9 pgs).

International Search Report for International Patent Application No. PCT/AU03/00759, filed Jun. 19, 2003.

International Search Report, International Application No. PCT/US05/34276, mailed Oct. 9, 2007.

International Search Report, International Application No. PCT/US2006/009978, mailed Jul. 13, 2006 (2 pgs).

Kimura, A.., et al., "Effects of Neutron Irradiation on the Transformation Behavior in Ti—Ni Alloys," Abstract, Proceedings of the Int'l Conf. on Mariensitic Transformations, 1992, pp. 935-940.

Nat'l Aeronautics and Space Administration, "55-Nitinol—The Alloy with a Memory: Its Physical Metallurgy, Properties, ans Applications," NASA Report, pp. 24-25.

Ramanathan, G., et al., "Experimental and Computational Methods for Shape Memory Alloys," 15th ASCE Engineering Mechanics Conference, Jun. 2-5, 2002.

Shabalovskaya, S., "Surface Corrosion and Biocompatibility Aspects of Nitinol as and Implant Material," Bio-Medical Materials and Engineering, 2002, vol. 12, pp. 69-109.

Uchil, J., "Shape Memory Alloys—Characterization Techniques," Pramana—Journal of Physics, 2002 vol. 58 (5)(6), pp. 1131-1139.

European Search Report from EP 11 17 6128.

* cited by examiner

SEPTAL CLOSURE DEVICES

CROSS-REFERENCE TO RELATED APPLICATION

This application claims priority from provisional Ser. No. 60/431,924, filed Dec. 9, 2002, which is incorporated herein by reference.

BACKGROUND OF THE INVENTION

A patent foramen ovale (PFO) as shown in FIG. 1 is a persistent, one-way, usually flap-like opening in the wall between the right atrium 10 and left atrium 12 of the heart. Since left atrial (LA) pressure is normally higher than right atrial (RA) pressure, the flap typically stays closed. Under certain conditions, however, RA pressure can exceed LA pressure, creating the possibility for right to left shunting that can allow blood clots to enter the systemic circulation.

In utero, the foramen ovale serves as a physiologic conduit for right-to-left shunting. After birth, with the establishment of pulmonary circulation, the increased left atrial blood flow and pressure results in functional closure of the foramen ovale. This closure is typically followed by anatomical closure of the two over-lapping layers of tissue, septum primum 14 and septum secundum 16. However, a PFO has been shown to persist in a significant minority of adults.

The presence of a PFO has no therapeutic consequence in otherwise healthy adults. But patients suffering a stroke or TIA in the presence of a PFO and without another cause of ischemic stroke are considered for prophylactic medical therapy to reduce the risk of a recurrent embolic event. These patients can be treated with oral anticoagulants, but such drugs have the potential for adverse side effects such as hemorrhaging, hematoma, and interactions with other drugs. In certain cases, such as when the use of anticoagulation drugs is contraindicated, surgery may be used to suture a PFO closed. Suturing a PFO requires attachment of septum secundum to septum primum with a stitch (continuous or interrupted), which is the common way a surgeon shuts the PFO under direct visualization.

Non-surgical closure of PFOs has become possible with umbrella devices and a variety of other similar mechanical closure designs developed initially for percutaneous closure of atrial septal defects (ASD). These devices allow patients to avoid the potential side effects often associated with anticoagulation therapies.

SUMMARY OF EMBODIMENTS OF THE INVENTION

Embodiments of the present invention are directed to devices for closing septal defects such as PFOs. The closure devices include proximal and distal occlusion members for applying compressive forces to tissue on opposite sides of septal defects to help close the defects. Material patches of a fabric or growth promoting matrix can optionally be applied to the occlusion members to cover the defect and promote tissue ingrowth to improve defect closure. The devices are collapsible for delivery and deployment, and can be easily retrieved and redeployed or repositioned if needed.

These and other features will become apparent from the following detailed description, wherein embodiments of the invention are shown and described by way of illustration. As will be realized, the invention is capable of other and different embodiments and its several details may be capable of modifications in various respects, all without departing from the invention. Accordingly, the drawings and description are to be regarded as illustrative in nature and not in a restrictive or limiting sense.

DETAILED DESCRIPTION

Various embodiments of the present invention are directed to methods and devices for closing septal defects such as PFOs. The devices apply compressive forces to compliant tissue on opposite sides of the defect to help close the defect.

Figure 1:
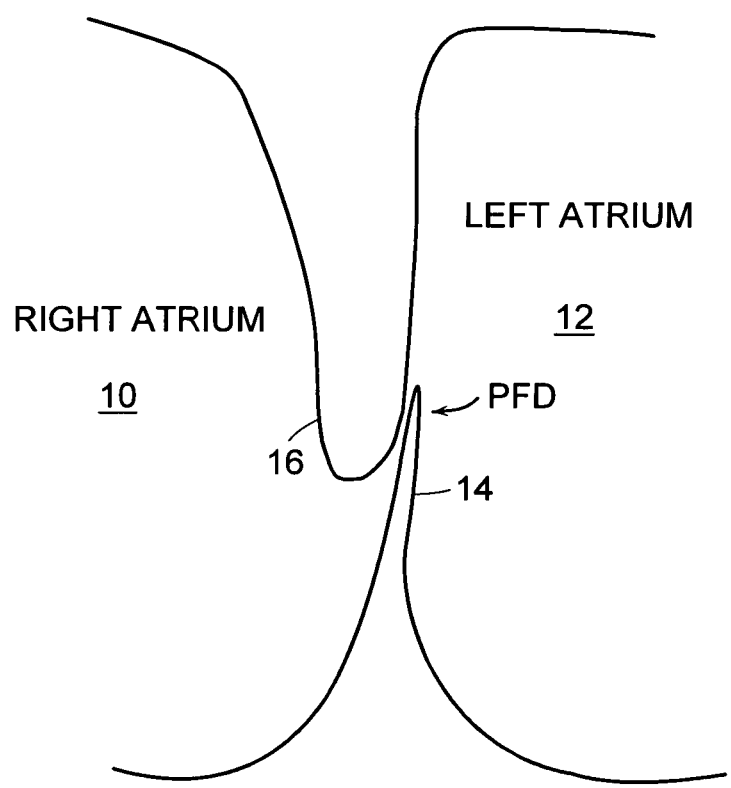
FIG. 1 is a cross-sectional view of a portion of the heart illustrating a PFO.
Figure 2A:
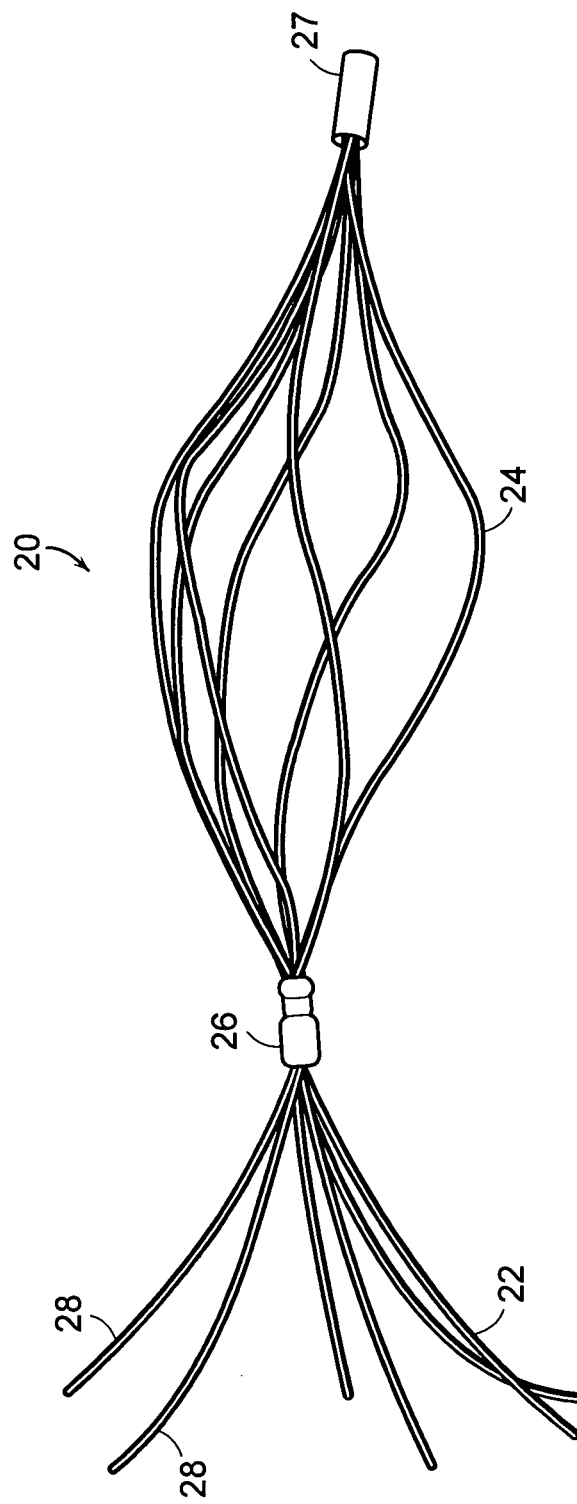
FIGS. 2A and 2B are perspective views of a closure device in accordance with one or more embodiments of the invention in generally collapsed and expanded states, respectively.
Figure 2B:
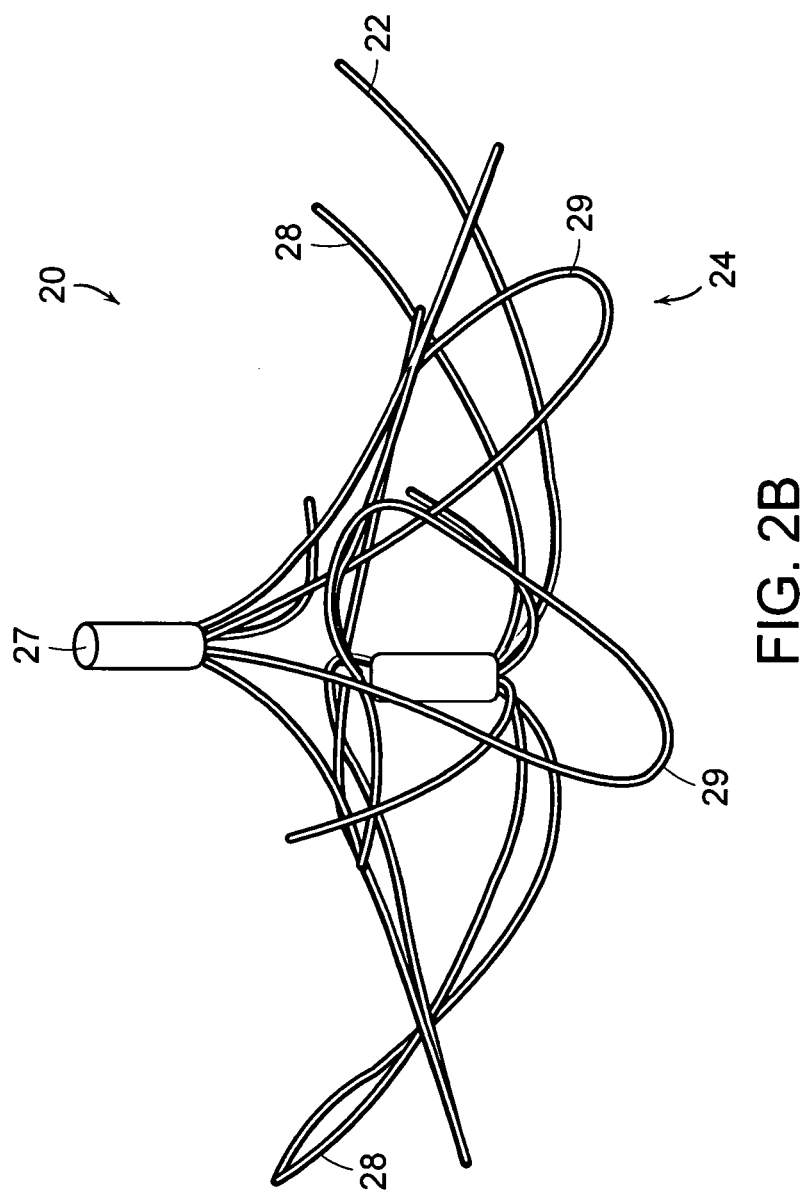

FIGS. 2A-2B and 3A-3D generally illustrate a closure device or occluder 20 in accordance with one or more embodiments of the invention. FIGS. 2A and 2B illustrate the device 20 in collapsed and expanded states, respectively. FIGS. 3A-3D illustrate a process of deploying the device 20. The device 20 is radially collapsible into a collapsed configuration (as shown in FIG. 2A) for delivery through a catheter and deployment. Upon deployment, it expands into a predefined expanded configuration (shown generally in FIG. 2B).

The device 20 includes an expandable distal occlusion member 22 and an expandable proximal occlusion member 24 connected to each other. The distal occlusion member 22 (which can be positioned on the left atrial side of a PFO) includes a framework having a central hub 26 and a plurality of outwardly extending elongated struts 28. The free ends of struts 28 can have small loops, ball tips, or otherwise be rounded or configured to reduce trauma. The proximal occlusion member 24 (which can be placed on the right atrial side of the PFO) includes a plurality of wires in the form of loops 29, shown here as overlapping, when the device 20 is in an expanded state. As shown in FIGS. 2A and 2B, loops 29 each extend from a central hub 26 to an end cap 27. The loop forms a plane that is approximately parallel to the tissue it is closing and applies a force that is generally perpendicular to the plane (see also FIG. 5A).

In accordance with some embodiments of the invention, material patches of a fabric or growth promoting matrix can optionally be applied to the occlusion members 22, 24. When the device 20 is deployed, the patches can cover the defect and promote tissue ingrowth to improve defect closure. Numerous biocompatible materials can be used for the patches including, but not limited to, polyester fabrics (such as knitted or woven polyester fabrics), GORE-TEX® (ePTFE), and IVALON® (polyvinyl alcohol foam), naturally occurring tissue scaffolds (such as collagen or acellular tissue matrices), polyurethane, bioresorbable tissue matrices, or electrospun fabric.

The wires forming the device are preferably made of a thermally responsive material having shape memory properties (e.g., nitinol, nitinol alloys, shape memory polymeric materials). The wires could be made of a bioresorbable materials if a tissue scaffold is provided. Suitable shape memory materials can include a first, relatively pliable low temperature phase (mainly R-phase or martensite or both) and a second, relatively rigid high temperature phase (mainly austenite). Such material can, e.g., have a high temperature phase at about body temperature or, more preferably, at temperatures above about 70° F. As is generally known for such materials, the device is collapsed in the R-phase or martensite phase, and then recovers a programmed shape when body heat causes the material in the device to transition to its austenitic phase. It should be understood that these are representative properties that can be varied.

In some respects, this device resembles a vena cava filter as shown in U.S. Pat. No. 4,425,908. A vena cava filter is designed to be inserted into a major vein to prevent a blood clot from entering the lungs, a different purpose from that described here.

Figure 3A:
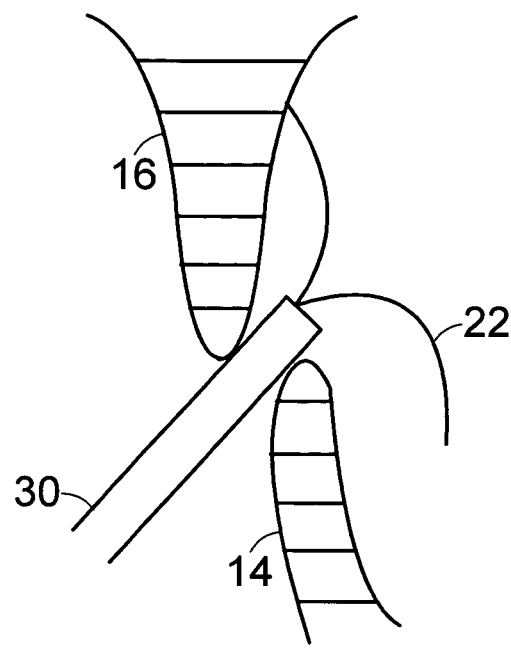
FIGS. 3A-3D are side views illustrating deployment of the closure device of FIGS. 2A and 2B in a PFO.
Figure 3B:
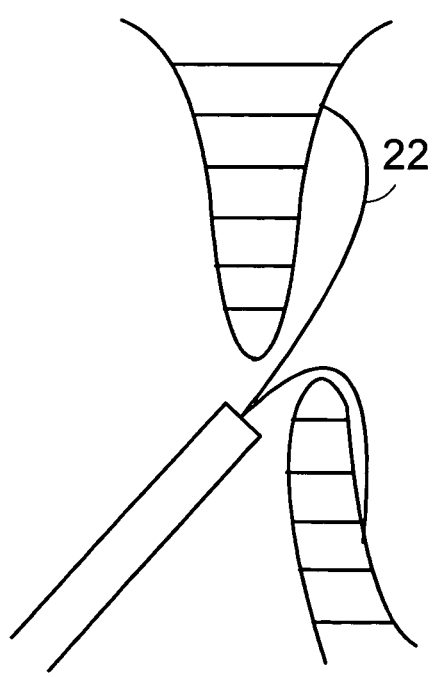
Figure 3C:
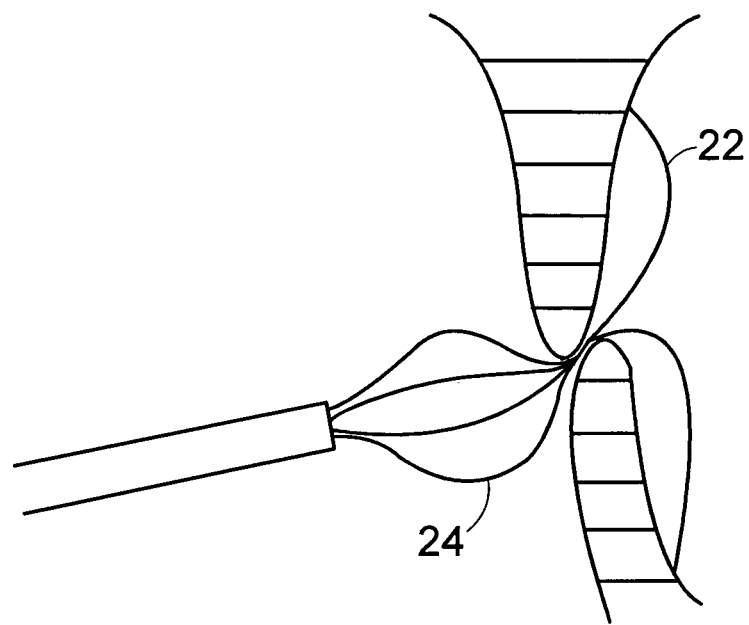
Figure 3D:
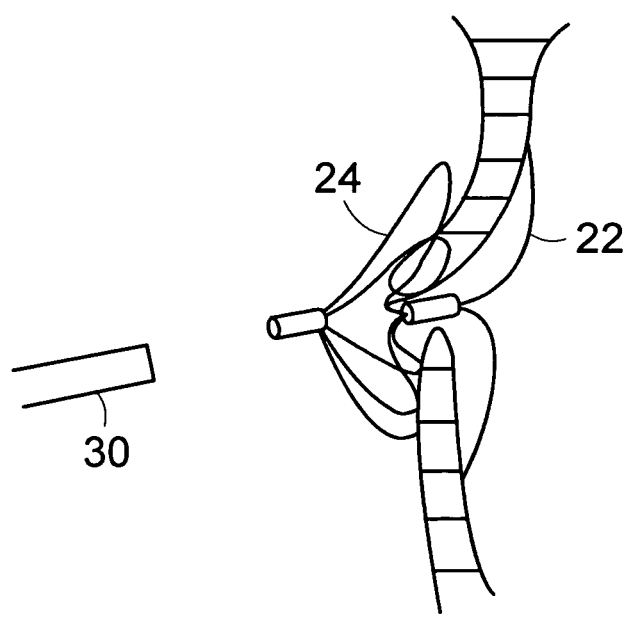

FIGS. 3A-3D illustrate deployment of the device 20 for closing a PFO. The device 20 can be delivered to the septal defect in the collapsed state through a standard catheter 30. The catheter 30 is passed through the defect between septum primum 14 and septum secundum 16 as shown in FIG. 3A. The distal occlusion member 22 is then deployed as shown in FIG. 3B. The catheter 30 is retrieved, and the proximal occlusion member 24 is deployed on the proximal part of the defect as shown in FIGS. 3C and 3D. Once deployed, compressive forces are applied by the device 20 to the tissue, causing septum secundum 16 to be drawn toward septum primum 14. A tissue scaffold, if provided, would cause tissue to grow around the scaffold. The device 20 remains in place while the defect can heal to close the hole.

As indicated in FIG. 3D, the struts can just contact tissue at their ends, while the loops generally contact tissue over more of the length of the loops. If desired, the device 20 can be easily retrieved and redeployed or repositioned. The device 20 can be fully or partially pulled back into the delivery sheath from the defect by pulling on end cap 27, which serves as the proximal attachment point of the occluder for use with a recovery type catheter. The device can then be removed completely from the body or redeployed.

Benefits of the device 20 include high fatigue resistance, ability to be used with small diameter delivery sheaths, reduced metal mass, ease of manufacturing, reduced cost, and overall design simplicity.

Figure 4A:
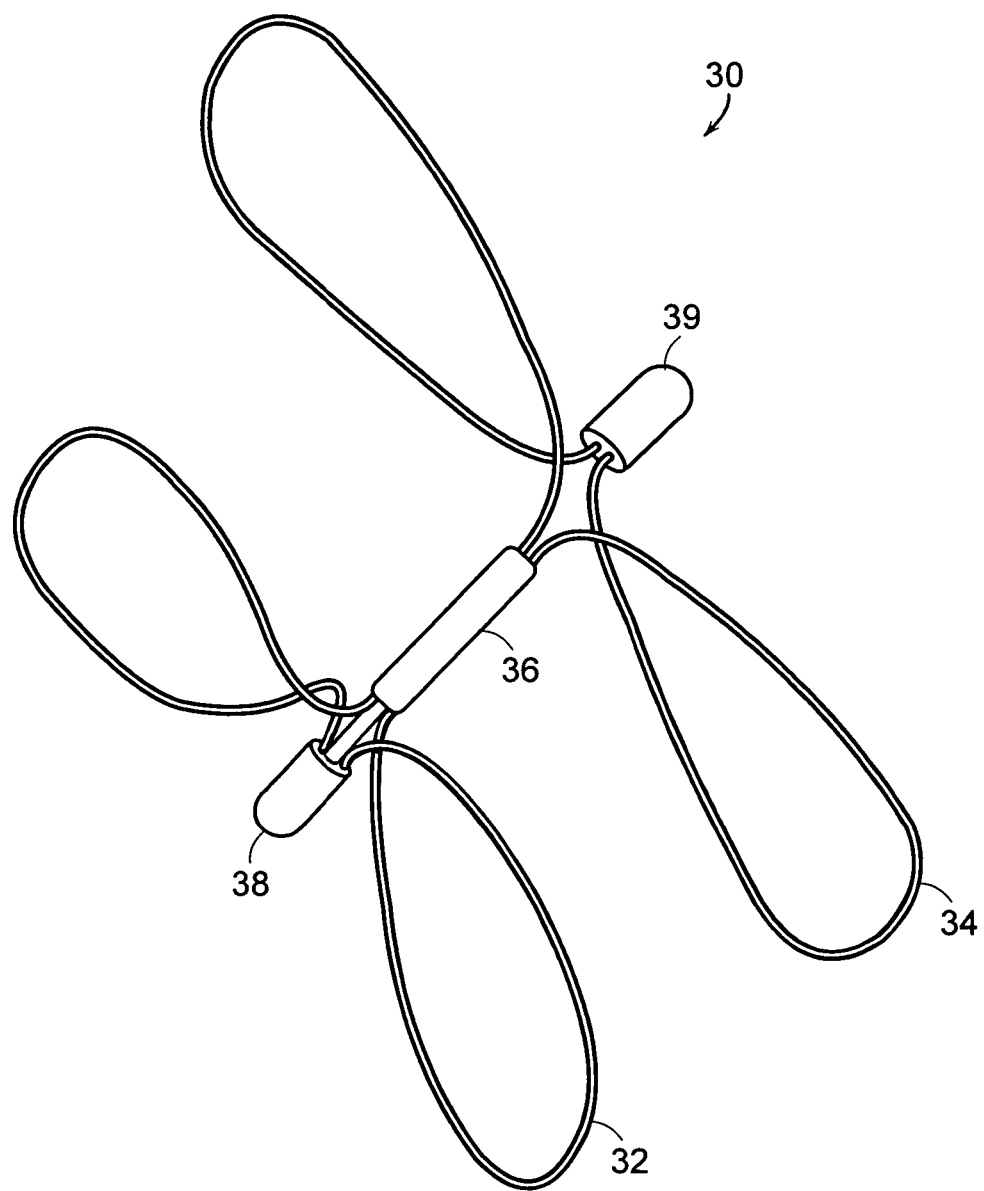
FIGS. 4A and 4B are perspective views of a closure device in expanded and collapsed states, respectively, in accordance with one or more further embodiments of the invention.
Figure 4B:
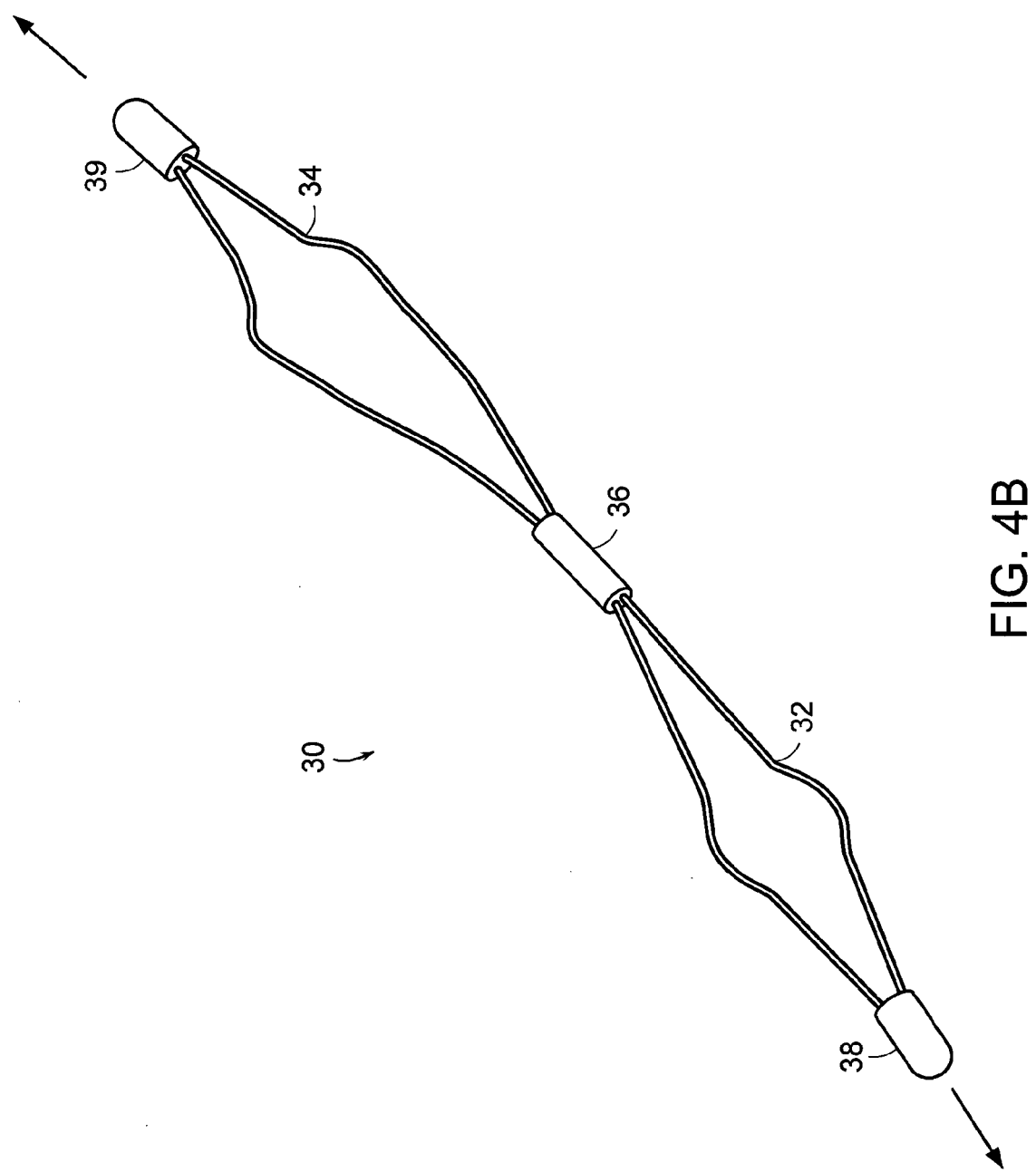

FIGS. 4A and 4B generally illustrate a closure device or occluder 30 in accordance with one or more further embodiments of the present invention. FIG. 4A illustrates the device 30 in an expanded state when deployed, and FIG. 4B illustrates the device 30 in a generally collapsed state for delivery through a catheter.

The device 30 includes a distal occlusion member 32 (which can be positioned on the left atrial side of a PFO) and a proximal occlusion member 34 (which can be placed on the right atrial side of the PFO). When deployed, the occlusion members 32, 34 apply compressive forces to both sides of a defect, sandwiching the compliant tunnel tissue closed.

Figure 5A:
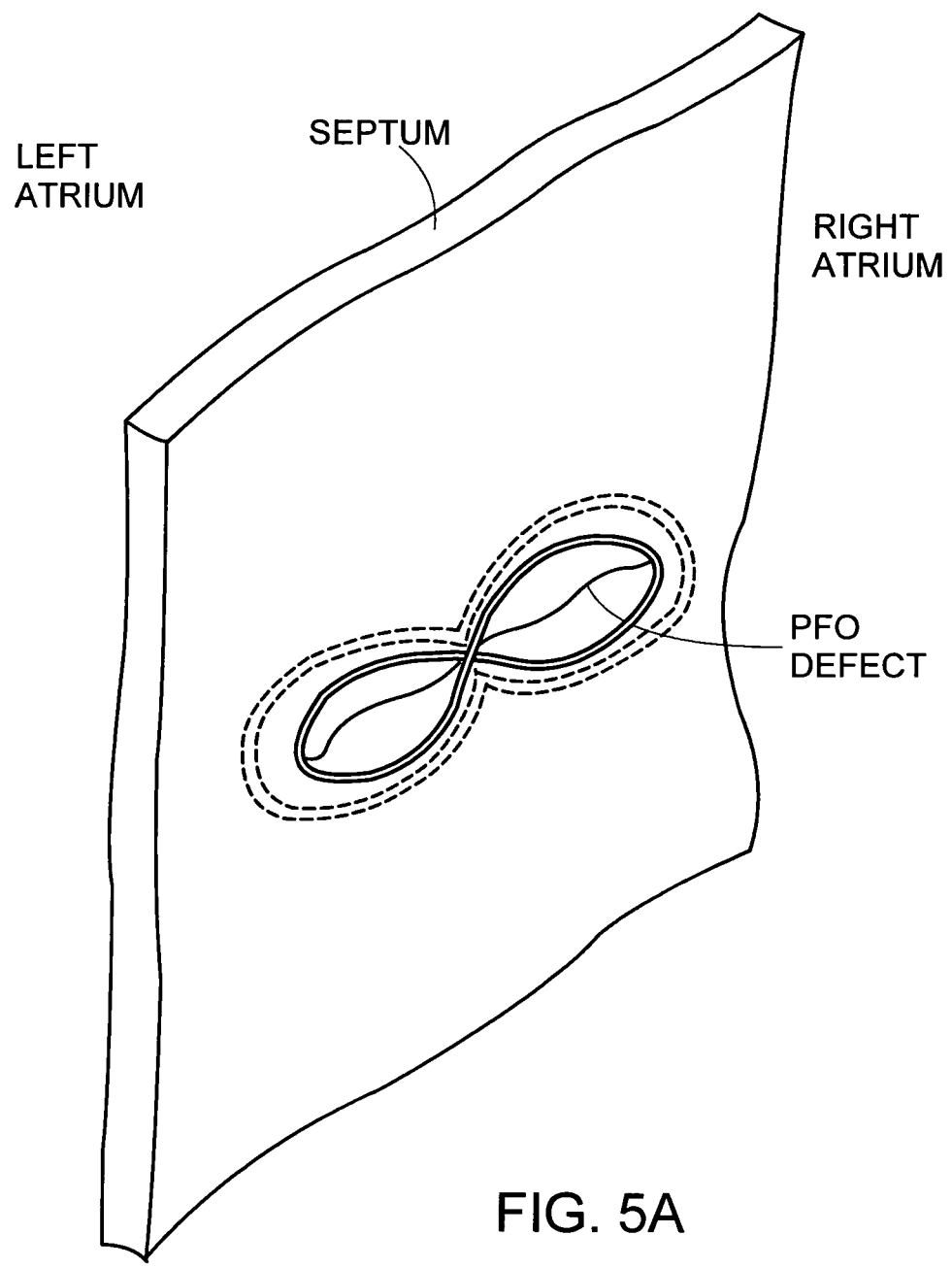
FIGS. 5A and 5B are perspective and side views, respectively, illustrating placement of the closure device of FIGS. 4A and 4B in a PFO.
Figure 5B:
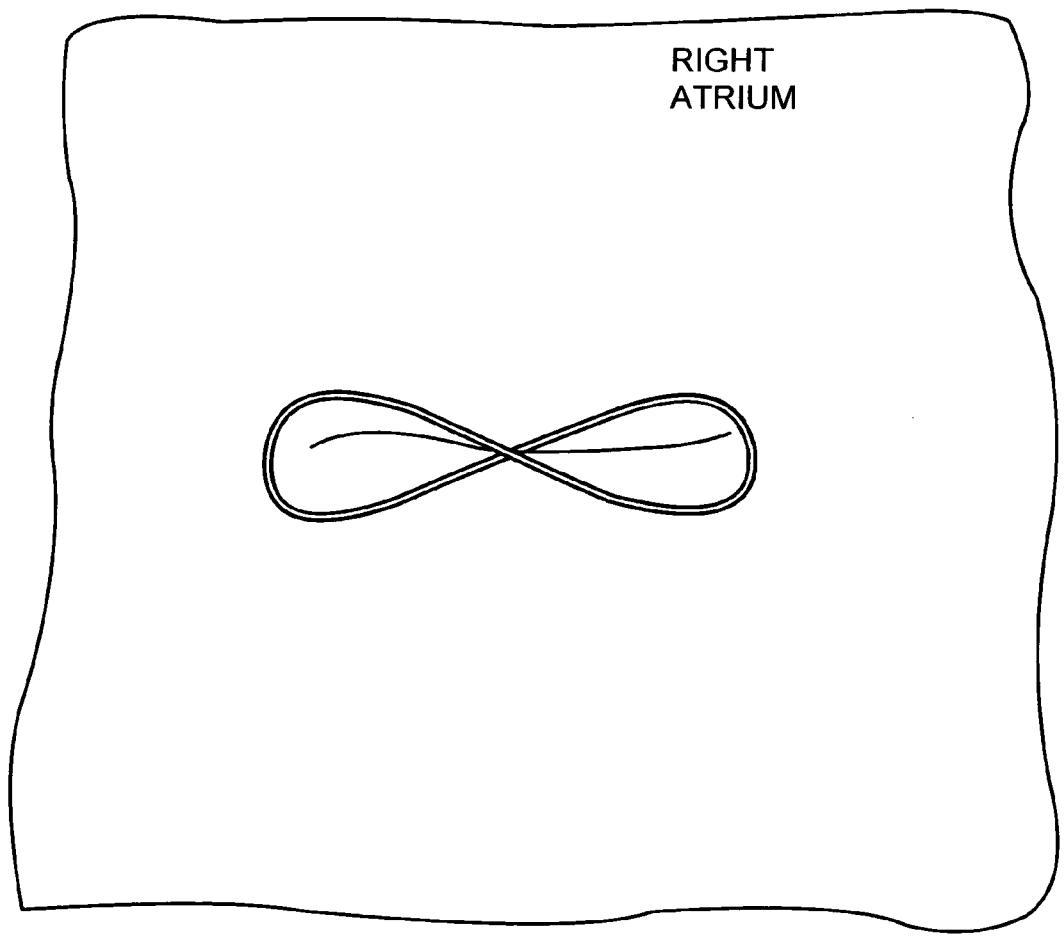

Each occlusion member 32, 34 in device 30 includes two collapsible propeller shaped wire petal members. The petals of the two occlusion members are joined by a connecting member 36, which extends into the tunnel defect when the device 30 is deployed. The loops that make up the propeller are shown extending from the central member 36 to end caps 38 and 39. These end caps, like the ones in the other embodiments, can be in a line with the connecting member 36 and can be perpendicular to septum primum and septum secundum if deployed to close a PFO; or they could be not in a line and/or could be skewed relative to a line perpendicular to septum primum and septum secundum if deployed to close a PFO The petals collapse when the device 30 is pulled at opposite ends as shown in FIG. 4B. This collapsibility allows the device 30 to be elongated for loading into a delivery catheter. Device delivery can be achieved percutaneously by advancing the delivery catheter through the PFO defect. The device 30 can then be deployed. The device can be placed as illustrated, e.g., in FIGS. 5A-5B, with the petals generally oriented in-line with the defect. As shown, a plane defined by a loop is generally parallel to each septum and substantially perpendicular to the force applied by the loop. In FIG. 5A, the left atrial petals are illustrated generally in dashed lines and can be in the same circumferential location.

The device is preferably made from a material having shape memory properties such as Nitinol. This thermally responsive material allows the device petals to attain their desired deployed state geometry once released from the delivery catheter. The petals can be suitably sized to ensure that the device applies sufficient force to achieve defect closure.

The device 30 can close a PFO by applying compressive forces to the compliant flaps of the PFO. In accordance with some embodiments, to further promote hole closure, a fabric or a growth promoting matrix, which may include growth factors or other pharmacological agents or cells, can optionally be added to the petals to promote tissue growth over the device to plug the hole.

The petal design of the device provides wide surface contact with cardiac tissue on both the left and right atrial sides of the PFO defect. Substantial surface area contact by the petals enables generally evenly distributed pressure to be applied to close the PFO. The relatively simple structure of the device 30 allows use of an implant having a reduced metal mass. The device design also facilitates easy manufacture. The device can be made, e.g., by crimping, welding, or otherwise joining the device together in the petal geometry and then annealing.

Figure 6:
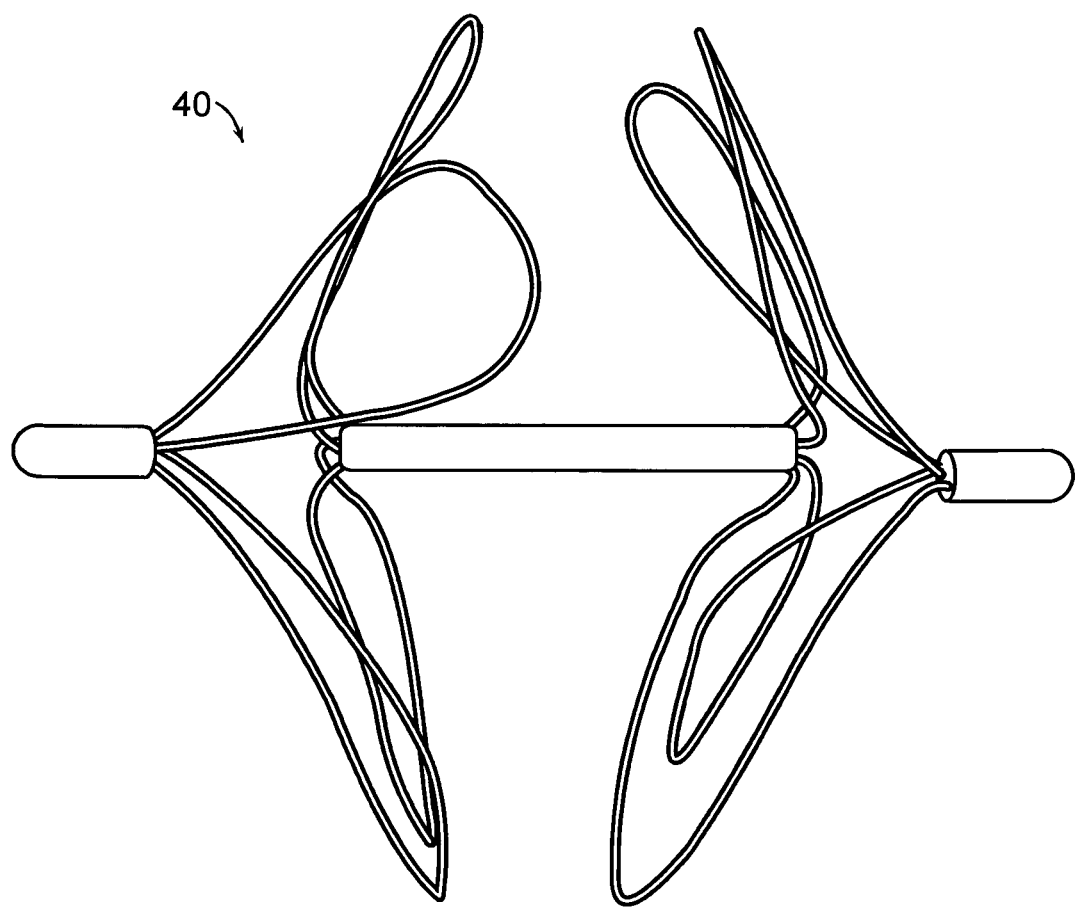
FIG. 6 is a side view of a closure device in accordance with one or more further embodiments of the invention.

While the FIG. 4 device 30 has two petals on each of the proximal and distal sides of the device, it should be understood that any number of petals can be used. For example, FIG. 6 illustrates a device 40 having more than two petals on each of the proximal and distal sides of the device. As shown in FIG. 6, the loops on one side are not necessarily at the same circumferential location as loops on the other side.

Having described various embodiments of the present invention, it should be apparent that modifications can be made without departing from the spirit and scope of the invention. The device is described for use with a PFO, but could be used for an atrial septal defect or a ventricular septal defect, in which case the device would typically have a tissue scaffold or other fabric.

What is claimed:

1. An apparatus comprising:
    a patent foramen ovale (PFO) closure device movable from a collapsed configuration when within a delivery device to a deployed configuration for providing compressive force to a septum primum and a septum secundum, the device further comprising:
    a central body for extending through the PFO, wherein the central body is elongated and substantially linear and extends along a longitudinal axis of the device,
    a first end cap, and a second end cap in line with the central body;
    at least a first wire and a second wire extending through the central body from the first end cap to the second end cap;

the first wire and the second wire defining a first occlusion member on a first side of the central body each wire of which extends in a substantially planar manner along the longitudinal axis of the device when in the collapsed configuration and forming a first and a second collapsible loop which are generally perpendicular to the longitudinal axis of the device and which extend in a first plane perpendicular to the central body when in the deployed configuration, and the first and second wire defining a second occlusion member on a second side of the central body, each wire of which extends in a substantially planar manner along the longitudinal axis of the device when in the collapsed configuration and forming a third and a fourth collapsible loop which are generally perpendicular to the longitudinal axis of the device and which extend in a second plane perpendicular to the central body when in the deployed configuration, wherein the first and second plane are generally parallel, wherein each collapsible loop is a single loop extending from the central body to the first or second end cap;

wherein moving the first end cap toward the central body moves the first occlusion member from the collapsed configuration to the deployed configuration and moving the second end cap moves the second occlusion member from the collapsed configuration to the deployed configuration;

wherein when in the deployed configuration, the first and second occlusion members each cooperate with the central body to apply a generally perpendicular force to overlapping layers of the septum primum and the septum secundum to close the PFO;

wherein each of the collapsible loops is independent from one another; and wherein further, the first wire and the second wire extending through the central body from the first end cap to the second end cap extend in a substantially planar manner along the longitudinal axis of the device when in the collapsed configuration within the delivery device.

2. The apparatus of claim 1, wherein the device includes nitinol.

3. The apparatus of claim 1, wherein the device includes a shape memory polymeric material.

4. The apparatus of claim 1, wherein the device is made from a shape memory material with properties such that the device, when delivered into a body, has a phase transition and assumes the deployed configuration.

5. The apparatus of claim 1, wherein the device is retrievable, redeployable, and repositionable.

6. A method comprising delivering the PFO closure device of claim 5 through a catheter to a PFO.

7. The apparatus of claim 1, further comprising a material over the first and second loops for promoting tissue ingrowth.

8. The apparatus of claim 7, wherein the loops are made of a bioresorbable material.

9. A method comprising delivering the PFO closure device of claim 8 through a catheter to a PFO.

10. A method comprising delivering the PFO closure device of claim 8 through a catheter to a PFO, and drawing the device back into the catheter.

11. The apparatus of claim 7, further comprising a material over the third and fourth loops for promoting tissue ingrowth.

12. A method comprising delivering the PFO closure device of claim 7 through a catheter to a PFO.

13. A method comprising delivering the PFO closure device of claim 1 through a catheter to a PFO.

14. The method of claim 13, further comprising aligning a first axis defined by the first and second loops when in the deployed configuration with a longitudinal axis defined by the septum primum and septum secundum, wherein the first axis extends from a point on the first loop furthest from the central body to a point on the second loop furthest from the central body.

15. The method of claim 14, further comprising aligning a second axis defined by the third and fourth loops when in the deployed configuration with the longitudinal axis defined by the septum primum and septum secundum, wherein the second axis extends from a point on the third loop furthest from the central body to a point on the fourth loop furthest from the central body.

16. A method comprising delivering the PFO closure device of claim 1 through a catheter to a PFO, wherein the device includes a shape memory material.

17. The apparatus of claim 1, wherein each loop is petal shaped.

* * * * *